United States Patent [19]

Morrison, Jr. et al.

[11] 4,303,790

[45] Dec. 1, 1981

[54] 2-AMINO-4-IMINO-6-HYDRAZINOPYRIMIDINE

[75] Inventors: Robert W. Morrison, Jr.; William R. Mallory; Virgil L. Styles, all of Raleigh, N.C.

[73] Assignee: Burroughs Wellcome Co., Research Triangle Park, N.C.

[21] Appl. No.: 153,060

[22] Filed: May 27, 1980

Related U.S. Application Data

[62] Division of Ser. No. 922,545, Jul. 7, 1978, Pat. No. 4,225,710.

[30] Foreign Application Priority Data

Jul. 8, 1977 [GB] United Kingdom ............... 28765/77

[51] Int. Cl.$^3$ .................. A61K 31/505; C07D 239/50
[52] U.S. Cl. ..................................... 544/323; 424/251; 544/236; 544/256; 544/258; 544/264; 544/320; 544/321
[58] Field of Search ......................................... 544/323

[56] References Cited

U.S. PATENT DOCUMENTS

| | | | |
|---|---|---|---|
| 2,328,956 | 9/1943 | D'Alelio et al. | 544/323 |
| 2,435,203 | 2/1948 | D'Alelio et al. | 544/323 |
| 3,461,461 | 8/1969 | Anthony et al. | 544/323 |
| 3,464,987 | 9/1969 | Ursprung et al. | 544/323 |
| 3,998,827 | 12/1976 | Thomas, Jr. et al. | 544/323 |
| 4,255,427 | 3/1981 | Morrison, Jr. et al. | 544/323 |

*Primary Examiner*—Donald G. Daus
*Assistant Examiner*—James H. Turnipseed
*Attorney, Agent, or Firm*—Donald Brown

[57] ABSTRACT

The present invention provides pyrimido(4,5-c)pyridazines, to methods for preparing them, formulations containing them and the preparation of such formulation and the use of such compounds in human therapy. These pyrimido(4,5-c)pyridazines of this invention are useful due to their activity as inhibitors of dihydropteroic and biosynthesis.

1 Claim, No Drawings

2-AMINO-4-IMINO-6-HYDRAZINOPYRIMIDINE

This is a division, of application Ser. No. 922,545 filed July 17, 1978 now U.S. Pat. No. 4,225,710.

This invention relates to pyrimido(4,5-c)-pyridazines, their methods of synthesis, formulations containing them and their use as inhibitors of dihydropteroic acid biosynthesis (DHPB).

The first pyrimido(4,5-c)pyridazines were disclosed by Pfeiderer and Ferch in 1958, *Ann. Chem.*, 615, 48 (1958) but no pharmacological activity was disclosed for these compounds which have the formula (I):

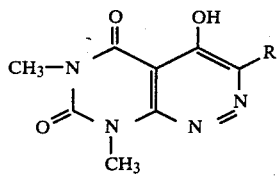

wherein R is a hydrogen atom or $-CO_2C_2H_5$ group. We have now discovered a group of pyrimido(4,5-c)pyridazines which are useful as inhibitors of dihydropteroic acid biosynthesis (DHPB).

The present invention provides novel pyrimido (4,5-c)pyridazines of formula (II), or their tautomers, or salts thereof,

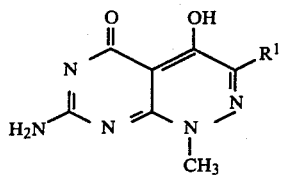

wherein $R^1$ is a lower alkyl group, a hydroxymethyl group, a phenyl group, a carboxy group, a benzyl group optionally substituted in the phenyl ring with one or more nitro or lower alkoxy groups, a phenacyl group optionally substituted in the phenyl ring with one or more hydroxy or lower alkoxy groups, a lower acyloxymethyl group, an indolyl or indolylmethyl group, a group $CH(CN)CH_2C_6H_5$ optionally substituted in the phenyl ring with one or more lower alkoxy groups, a group $CH(Y)CO_2Z$ or a group $CH_2CH_2CO_z$ in which Y is a hydrogen atom or a lower alkyl or alkoxy group and Z is a hydrogen atom or a lower alkyl group.

The term "lower" as used herein in conjunction with an alkyl, alkoxy or acyl group is indicative of the fact that such groups have from 1 to 6 carbon atoms arranged in a straight or branched chain. The expression "phenacyl group" however is used to denote solely a $C_6H_5COCH_2$ - group.

It is to be understood that compounds where tautomerism is possible between, on the one hand, a hydroxy group and an oxo group, and on the other hand, an amino group and an imino group, at a particular position in either of the rings of the pyrimido(4,5-c)-pyridazines of formula (II), the more stable forms are respectively, the oxo group and the amino group. However, the general formulae used in the present specification do not necessarily represent the more stable forms of such pyridazines.

The above compounds of formula (II) inhibit the enzyme dihydropteroatesynthetase which enables microorganisms to synthesise an essential intermediate in the production of tetrahydrofolate co-factors. Most of these co-factors are one-carbon adducts of tetrahydrofolic acid and they are essentially metabolites in cells for the biosynthesis of purines, thymidylic acid, serine, and several other biologically important compounds. Man and other higher animals are unable to synthesise such co-factors and therefore they have to obtain them from food which contains the required preformed folates.

On the other hand, microorganisms synthesise the co-factors themselves from simpler chemicals. Generally the biosynthetic process first provides 'dihydropteridine' (Pt), i.e. 2-amino-4-hydroxy-6-hydroxymethyl-7,8-dihydropteridine (HMPt) pyrophosphate ester, from its immediate precursor HMPt in the presence of the enzyme hydroxymethyldihydropteridine pyrophosphokinase (HMPPs). Pt then condenses with p-aminobenzoic acid (pAB) in the presence of the enzyme dihydropteroatesynthetase to form dihydropteroic acid (DPtA). This intermediate further condenses with a glutamate to form dihydrofolic acid (DFA or 'folate') which is then enzymatically reduced to produce the essential tetrahydrofolate. It is in the formation of DPtA from pAB and Pt that the present compounds have inhibitory activity.

On the basis of such inhibitory activity the pyrimido(4,5-c)pyridazines of formula (II) have anti-microbial, in particular anti-bacterial, activity.

Within the class of pyrimido(4,5-c)pyridazines of formula (II) there is a group of compounds which are particularly active and these have $R^1$ as a methyl group, a phenyl group, a benzyl group optionally substituted in the phenyl ring with a nitro or 2 or 3 methoxy groups, a hydroxymethyl group, a phenacyl group optionally substituted in the phenyl ring with a hydroxy group, or 2 or 3 methoxy groups, a group $CH_2CH_2CO_2H$, an acetyloxymethyl group, an indolylmethyl group or a group $CH(CN)CH_2C_6H_5$ substituted in the phenyl ring with 3 methoxy groups, a group $CH(Y)CO_2Z$ in which Y is a methyl group, methoxy group or a hydrogen atom and Z is a hydrogen atom, or a $C_{1-4}$ alkyl group.

As examples of compounds which are particularly active and which fall within this class are 7-amino-1,3-dimethyl-4-oxo-5-hydroxy-1,4-dihydropyrimido(4,5-c)-pyridazine; 7-amino-1-methyl-3-phenyl-4-oxo-5-hydroxy-1,4-dihydropyrimido(4,5-c)pyridazine; 7-amino-1-methyl-3-hydroxymethyl-4-oxo-5-hydroxy-1,4-dihydropyrimido(4,5-c)pyridazine; 7-amino-1-methyl-3-benzyl-4-oxo-5-hydroxy-1,4-dihydropyrimido(4,5-c)pyridazine; 7-amino-1-methyl-3-(2-nitrobenzyl)-4-oxo-5-hydroxy-1,4-dihydropyrimido(4,5-c)pyridazine; 7-amino-1-methyl-3-indolylmethyl-4-oxo-5-hydroxy-1,4-dihydro-pyrimido(4,5-c)pyridazine; 7-amino-1-methyl-3-acetoxymethyl-4-oxo-5-hydroxy-1,4-dihydropyrimido(4,5-c)-pyridazine; 7-amino-1-methyl-3-(1-carboxyethyl)-4-oxo-5-hydroxy-1,4-dihydropyrimido(4,5-c)pyridazine; 7-amino-1-methyl-3-(2-carboxymethyl)-4-oxo-5-hydroxy-1,4-dihydropyrimido(4,5-c)pyridazine; 7-amino-1-methyl-3-(ethoxy-carbonylmethyl)-4-oxo-5 -hydroxy-1,4-dihydropyrimido-(4,5-c)pyridazine; 7-amino-1-methyl-3-(1-methoxy)-carboxymethyl)-4-oxo-5-hydroxy-1,4-dihydropyrimido-(4,5-c)pyridazine; 7-amino-1-methyl-3-(α-cyano-3,4,5-trimethoxyphenethyl)-4-oxo-5-hydroxy-1,4-dihydropyrimido(4,5-c)pyridazine; and especially 7-amino-1-methyl-3-(1-ethoxycarbonylethyl)-4-oxo-5-hydroxy-1,4-dihydropyrimido(4,5-c)pyridazine.

However, a more preferred class of even higher activity compounds, are those of formula (II) wherein $R^1$ is a benzyl group or especially wherein $R^1$ is a phenacyl group optionally substituted in the phenyl ring with a hydroxy group or 2 or 3 methoxy groups. Examples of compounds falling within this most preferred class are 7-amino-3-benzoylmethyl-1-methyl-4-oxo-5-hydroxy-1,4-dihydropyrimido(4,5-c)pyridazine; 7-amino-3-(3,4-dimethoxybenzoyl)methyl-1-methyl-4-oxo-5-hydroxy-1,4-dihydropyrimido(4,5-c)pyridazine; 7-amino-3-(3,4,5-trimethoxybenzoyl)methyl-1-methyl-4-oxo-5-hydroxy-1,4-dihydropyrimido(4,5-c)pyridazine; 7-amino-3-(3,4,5-trimethoxybenzoyl)methyl-1-methyl-4-oxo-5-hydroxy-1,4-dihydropyrimido(4,5-c)pyridazine; 7-amino-3-(2,4-dimethoxybenzoyl)methyl-1-methyl-4-oxo-5-hydroxy-1,4-dihydropyrimido(4,5-c)pyridazine; 7-amino-3-(3,4,5-trimethoxybenzyl)-1-methyl-4-oxo-5-hydroxy-1,4-dihydropyrimido(4,5-c)pyridazine; 7-amino-3-(2,5-dimethoxybenzoyl)methyl-1-methyl-4-oxo-5-hydroxy-1,4-dihydropyrimido(4,5-c)pyridazine; 7-amino-3-(2,4,6-trimethoxybenzoyl)methyl-4-oxo-5-hydroxy-1,4-dihydropyrimido(4,5-c)pyridazine; 7-amino-3-(3-hydroxybenzoyl)-methyl-4-oxo-5-hydroxy-1,4-dihydropyrimido(4,5-c)-pyridazine; and 7-amino-3-(3,4-dimethoxybenzyl)-1-methyl-4-oxo-5-hydroxy-1,4-dihydropyrimido(4,5-c)pyridazine.

It has previously been stated that in 1958 Pfleiderer W. and Ferch H. (Justus Liebig's Ann. Chem., 1958, 615, 48) reported the preparation of 4-hydroxy-6,8-dimethylpyrimido(4,5-c)pyridazine-5,7-(<u>6H</u>, <u>8H</u>)-dione by the-cyclisation of glyoxylic acid ethyl ester-1,3-dimethyluracil-(4)-hydrazone. It has now been found that this cyclisation reaction can surprisingly be extended to a novel class of intermediates which have a number of different substituents. Thus the present invention further provides a method of preparing a compound of formula (II), or a tautomer or a salt thereof, as hereinbefore defined which process comprises the cyclisation of a compound of the formula (III):

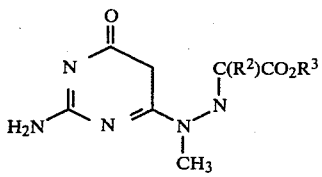

(III)

wherein $R^3$ is a lower alkyl group and $R^2$ is a lower alkyl group, a lower acyloxymethyl group, a phenyl group, a benzyl group optionally substituted in the phenyl ring with one or more nitro or lower alkoxy groups, a phenacyl group optionally substituted in the phenyl ring with one or more hydroxy or lower alkoxy groups, an indolyl or indolylmethyl group, a group $CH(CN)CH_2C_6H_5$ optionally substituted in the phenyl ring with one or more lower alkoxy groups, a group $CH(Y)CO_2Z$ or a group $CH_2CH_2CO_2Z$ in which Y is a hydrogen atom or a lower alkyl or alkoxy group and Z is a hydrogen atom or a lower alkyl group and thereafter optionally hydrolysing the lower acyloxymethyl group to a hydroxymethyl group.

Such is the nature of the substituents on the pyrimidine ring of the compounds of formula (III) that, unlike the above prior art teaching, ring closure can apparently only be achieved when the nitrogen atom at the 6-position is substituted as hereinabove. In other words, when this particular nitrogen atom is unsubstituted, corresponding compounds of formula (III) do not appear to cyclise. Moreover, this cyclisation reaction is particularly surprising since the report of Pfleiderer and Ferch teaches that such reactions only work for those hydrazone intermediates which have a glyoxylic acid alkyl ester substitution, yet a corresponding substitution in the present intermediates results in little, if any, pyrimido(4,5-c)pyridazine.

The reaction itself may be carried out in any suitable solvent but most desirably a hydroxylic solvent, for example glacial acetic acid, water, of $C_{1-4}$ alkanol, at reflux temperature for up to several days. Optimally, the reaction is carried out in refluxing methanol, or in ethanol at the reflux temperature of methanol. The hydrolysis of the lower acyloxymethyl group will preferably take place under alkaline conditions, for example, by using aqueous sodium hydroxide. The hydrolysis will be carried out at a non extreme temperature, i.e. between 10° and 100° C., and preferably at room temperature.

The compounds of formula (III) are novel and constitute a further aspect of this invention.

The compounds of formula (III) can be prepared, preferably in situ, by condensing a 2-amino-4-oxo-6-hydrazinopyrimidine of formula (IV) (or a tautomer thereof).

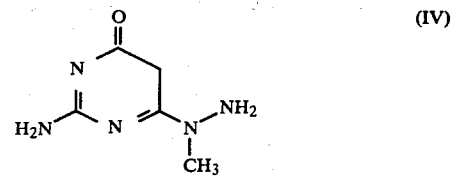

(IV)

with an α-keto ester of formula (V):

$$R^2CO.CO.OR^3 \qquad (V)$$

wherein $R^2$ and $R^3$ are as hereinbefore defined.

The preparation is suitably achieved using the conditions as specified for the cyclisation reaction above, for example by refluxing the reactants in methanol.

The compound of the formula (IV) are novel and constitutes a further aspect of this invention.

In the preparation of those compounds of formula (II), in which $R^1$ is a group $CH(Y)CO_2Z$, a group $CH_2CH_2CO_2Z$, or an optionally substituted phenacyl group, some other bi-cyclic compound may be formed as a by-product. In such instances it may be necessary to isolate the required compound by the usual procedures known in the art.

The compounds of formula (II) wherein $R^1$ is a group $CH(Y)CO_2Z$ or a group $CH_2CH_2CO_2Z$ in which Y is as hereinbefore defined and Z is a lower alkyl group may be hydrolysed to give further compounds of formula (II) wherein $R^1$ is a group $CH(Y)CO_2Z$ or a group $CH_2CH_2CO_2Z$ in which Y is as hereinbefore defined and Z is a hydrogen atom. The starting compounds of formula (II) may be prepared from the corresponding compound of formula (III) as described previously.

The conditions for this reaction are preferably alkaline which may be achieved by using, for instance, aqueous sodium hydroxide, and the reaction may be conveniently performed at room temperature for 15 to 150 minutes, for example 90 minutes.

Compounds of formula (II) wherein $R^1$ is other than an acyloxymethyl group or any group containing an ester function may be prepared by the hydrolysis of a compound of formula (VI):

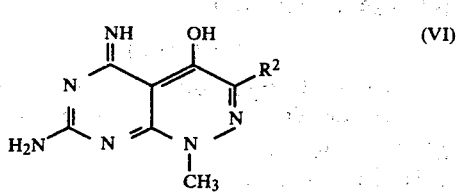

wherein $R^2$ is as hereinbefore defined.

The conditions for this reaction are preferably alkaline which may be achieved by using, for instance, aqueous sodium hydroxide, and the reaction may be conveniently performed under reflux for 10 to 40 hours, for example 24 hours. However, it should be noted that during the course of this reaction some decarboxylation may take place, possibly giving rise to small amounts of by-products which may necessitate subsequent separation by known methods.

This hydrolysis reaction is not preferred for those compounds of the formula (VI) wherein $R^2$ is a group which may undergo hydrolytic cleavage, for example when $R^2$ is an optionally substituted phenacyl group if it is desired to prepare a compound of the formula (II) having the substituent $R^1$ corresponding to $R^2$.

The compounds of formula (VI) are novel and constitute a yet further aspect of the present invention.

The compounds of formula (VI), may be prepared by the cyclisation of a compound of formula (VII):

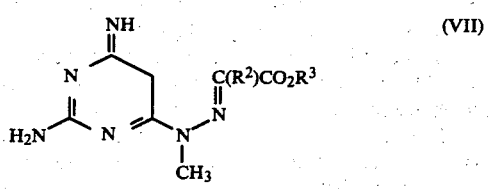

wherein $R^2$ and $R^3$ are as hereinbefore defined.

The reaction may be carried out in any suitable solvent but most desirably a hydroxylic solvent, for example glacial acetic acid, water, or $C_{1-4}$ alkanol, at reflux temperature for up to several days. Optimally, the reaction is carried out in refluxing methanol, or in ethanol at the reflux temperature of methanol.

The compounds of formula (VII) are novel and constitute a further aspect of the present invention.

The compounds of formula (VII) can be prepared, preferably in situ, by condensing a 2-amino-4-imino-6-hydrazinopyrimidine of formula (VIII), or a tautomer thereof,

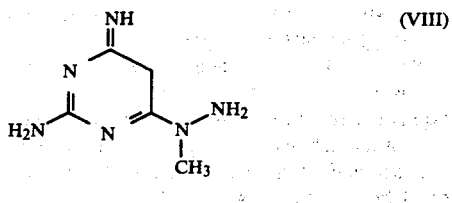

with an α-keto ester of formula (V).

The compound of formula (VIII) its tautomers and salts thereof are novel and provide a further aspect of the invention.

The preparation is suitably achieved using the conditions as specified for the cyclisation reaction immediately above, for example by refluxing the reactants in methanol.

In the preparation of those compounds of formula (VI) in which $R^2$ is a group $CH(Y)CO_2Z$, a group $CH_2CH_2CO_2Z$ or an optionally substituted phenacyl group, some other bicyclic compound may be formed as a by-product. In such instances it may be necessary to isolate the required compound by the usual procedures known in the art.

It should be noted that although, in general, hydrolysis of a compound of formula (VI) results in a correspondingly substituted compound of formula (II) except that the 5-position is oxo rather than imino substituted; in the case wherein $R^2$ in the starting material is a group $CH(Y)CO_2Z$ or a group $CH_2CH_2CO_2Z$ in which Z is a lower alkyl group, Z in the end-product of formula (II) is a hydrogen atom.

All the starting materials specified above for the various syntheses may be prepared by standard methods taught in the art.

The compounds of formula (II), or their tautomers, or pharmaceutically acceptable salts thereof may be presented in association with a carrier in pharmaceutical formulations suitable for parenteral, topical, rectal or oral administration. The formulations for oral or rectal administration are advantageously presented in discrete units, such as tablets, capsules, cachets, ampoules or suppositories, each containing a predetermined amount of compound, but may also be presented as a powder, as granules, as a solution or suspension in an aqueous or non-aqueous liquid, or as an ointment or paste for topical administration. For parenteral use, the formulations incorporating an aqueous or non-aqueous liquid carrier must be sterile and be presented in sealed containers. The formulations may be made by any of the known methods and may include one or more of the following accessory ingredients: diluents, solutes to render the solution isotonic with the blood, buffers, flavouring, binding, dispersing, surface-active, thickening, lubricating and coating materials, preservatives, bacteriostats, antioxidants, suppository and ointment bases, and any other acceptable excipients.

In another aspect of the present invention, therefore, there is provided a pharmaceutical formulation comprising a compound of formula (II) in combination with a pharmaceutically acceptable carrier. In yet another aspect the present invention provides a method of making a pharmaceutical formulation by admixing the compound of formula (II) with a carrier by known techniques.

The compounds of formula (II), for use alone, may be presented in the form of their pharmaceutically acceptable salts. Examples of pharmaceutically acceptable salts are those derived from mineral or organic acids, for example hydrochloric acid, hydrobromic acid, sulphuric acid, acetic acid, citric acid, tartaric acid, lactic acid, maleic acid, or salicyclic acid. Acid addition salts which are not pharmaceutically acceptable may be rendered so by a conventional metathetical reaction. Further examples of pharmaceutically acceptable salts are, in the case when $R^1$ in formula (II) is a carboxy group, a group $CH(Y)CO_2Z$, or a group $CH_2CH_2CO_2Z$ in which Z is a hydrogen atom, are alkali metal, for example sodium, salts.

In yet another aspect, the present invention provides a method of treating humans and other animals suffering from microbial infections which comprises administering a non-toxic effective antimicrobial treatment amount of a compound of formula (II), or preferably administering a pharmaceutical formulation comprising the said amount of a compound of formula (II) and a pharmaceutically acceptable carrier, to the infected human or other animal.

The compounds of formula (II) may be administered at a dose range of 1 to 60 mg/kg bodyweight daily in one or several doses.

Further advantages of the present invention can be ascertained from the following examples which should not be construed as limiting the scope of the invention in any way.

EXAMPLE 1

6-(1-Methylhydrazino)isocytosine (IV)

A mixture of 6-chloroisocytosine (17.50 g) and methylhydrazine (27.70 g) in water (900 ml) was stirred and refluxed for 3 hours. The resulting solution was allowed to stand at room temperature for 6 hours then at 0° C. overnight, in order that the product could crystallise out. The white crystals were collected by filtration, washed with water (800 ml) and subsequently with 95% ethanol (200 ml). Drying under vacuum at 70° C. yielded 6-(1-methylhydrazino)isocytosine (11.01 g; 56% of theoretical yield; m.p. 274°–280° C. decomposition).

Elemental analysis: Calcd. for $C_5H_9N_5O.0.5H_2O$: C, 36.58%; H, 6.14%; N, 42.66%. Found: C, 36.42%; H, 6.06%; N, 42.61%. nmr (DMSO-$d_6$) δ 3.12(s, 3H), 4.47(br s, 2H), 5.00(s, 1H), 6.16(br s, 2H), 9.68(br s, 1H). uv λ max ($CH_3OH$) 225.5 nm (ε24,000), 274(17,300).

EXAMPLE 2

7-Amino-1,3-dimethylpyrimido(4,5-c)pyridazine-4,5-(1H, 6H)-dione (II) ($R^1=CH_3$)

To a stirred, refluxing solution of 6-(1-methylhydrazino)isocytosine hemihydrate (8.00 g) in water (1 L) was added methyl pyruvate (6.00 g). After 70 minutes a greenish-yellow solid was collected by filtration of the hot reaction mixture, washed with two portions of water (50 ml each) and dried under vacuum at 70° C. to yield 7-amino-1,3-dimethylpyrimido(4,5-c)pyridazine-4,5-(1H, 6H)-dione (5.11 g; 51% of theoretical yield; m.p. >300° C.).

Elemental analysis: Calcd. for $C_8H_9N_5O_2$: C, 46.37%; H, 4.38%; N, 33.80%. Found: C, 46.48%; H, 4.42%; N, 33.91%. nmr (DMSO-$d_6$) δ 2.07(s, 3H), 3.71(s, 3H), 7.12(br s, 2H), 10.75(br, s, 1H) p$K_a$ values 4.1±0.1; 8.6±0.1 u.v. λ max ($CH_3OH$) 255 nm (ε40,000), 299.5(7,600), 310 sh (5,600).

EXAMPLE 3

7-Amino-3-acetoxymethyl-1-methylpyrimido(4,5-c)pyridazine-4,5(1H, 6H)-dione (II) ($R^1=CH_3CO.O.CH_2$)

To a stirred, refluxing solution of 6-(1-methylhydrazino)isocytosine hemihydrate (0.16 g) in methanol (5 ml) was added methyl 3-acetoxy-2-oxo-propanoate (0.19 g). After refluxing for a further 22 hours, the solid formed during the course of the reaction was collected by filtration of the hot reaction mixture and washed with methanol to yield 7-amino-3-acetoxymethyl-1-methylpyrimido(4,5-c)-pyridazine-4,5(1H, 6H)-dione (0.11 g; 43% of theoretical yield; m.p. >280° C.).

Elemental analysis: Calcd. for $C_{10}H_{11}N_5O_4$: C, 45.28%; H, 4.18%; N, 26.41%. Found: C, 45.11%; H, 4.24%; N, 26.37%. nmr (TFA) δ2.32(s, 3H), 4.27(s, 3H), 5.51 (s, 2H), 7.25(br, s, 2H). uv λ max ($CH_3OH$) 258 nm (ε37,100), 299.5(57,400).

EXAMPLE 4

7-Amino-3-hydroxymethyl-1-methylpyrimido(4,5-c)pyridazine-4,5(1H, 6H)-dione Sodium Salt (II) ($R^1=CH_2OH$)

To 7-amino-3-acetoxymethyl-1-methylpyrimido(4,5-c)-pyridazine-4,5(1H, 6H)-dione (0.100 g) in water (1 ml) was added dropwise with shaking 10% (w/w) aqueous sodium hydroxide (0.25 ml), the orange solution becoming quickly cloudy. The mixture was allowed to stand at room temperature for 30 minutes after which time the off-white granular solid which had formed was collected by filtration, rinsed well with methanol and dried under vacuum at room temperature to yield 7-amino-3-hydroxymethyl-1-methylpyrimido(4,5-c)pyridazine-4,5(1H, 6H)-dione as its sodium salt (0.082 g; 81% of theoretical yield; m.p. >300° C.).

Elemental analysis: Calcd. for $C_8H_8N_5NaO_3.H_2O$: C, 36.50%; H, 3.83%; N, 26.61%; Na, 8.73; Found: C, 36.55%; H, 3.91%; N, 26.50%, Na, 8.70. nmr (TFA) δ 4.29 (S, 3H), 5.19(s, 2H), 7.20(br s, 2H). uv λ max (0.1 N HCl) 255 nm (ε 39,400), 299(7,200).

EXAMPLE 5

7-Amino-3-(1-ethoxycarbonylethyl)-1-methylpyrimido(4,5-c)-pyridazine-4,5(1H, 6H)-dione (I) $R^1=CH(Y)CO_2Z$; $Z=C_2H_5$; $Y=CH_3$)

To a stirred, refluxing solution of 6-(1-methylhydrazino)isocytosine hemihydrate (1.86 g) in water (120 ml) was added diethyl 3-methyl-2-oxo-succinate (4.59 g). After refluxing for a further 3 hours, the solid formed during the course of the reaction was collected by filtration of the hot reaction mixture, washed with two portions of water (20 ml each) and dried under vacuum at 70° C. to yield 7-amino-3-(1-ethoxycarbonylethyl)-1-methylpyrimido(4,5-c)pyridazine-4,5(1H, 6H)-dione (1.93 g; 58% theoretical yield; m.p.>280° C.).

Elemental analysis: Calcd. for $C_{12}H_{15}N_5O_4$: C, 49.14%; H, 5.16%; N, 23.88%. Found: C, 49.10%; H,5.18%; N,23.62%. nmr (TFA) δ 1.38 (t, 3H), 1.77(d, 3H), 4.28 (s, 3H), 4.41(q, 3H), 7.17(br s, 2H). uv λ max ($CH_3OH$) 257 nm (ε 41,100), 299.5(7,400), 310 sh (5,600).

EXAMPLE 6

7-Amino-3-(1-carboxyethyl)-1-methylpyrimido(4,5-c)-pyridazine-4,5(1H, 6H)-dione Disodium Salt (II) ($R^1=CH(Y)CO_2Z$; $Y=CH_3$; $Z=H$)

A. A mixture of 7-amino-3-(1-ethoxycarbonylethyl)-1-methylpyrimido(4,5-c)pyridazine-4,5(1H, 6H)-dione (2.97 g) in 10% (w/w) aqueous sodium hydroxide (67 ml) was swirled vigorously for 25 minutes. Although a complete solution was not obtained during the agitation, a solid began to precipitate after 20 minutes. The mixture was then allowed to stand at room temperature for 1 hour before being chilled at 0° C. for 1½ hours to allow complete precipitation of the product. The precipitate was collected by filtration, washed with three portions of 95% ethanol (25 ml each) and dried overnight at room temperature in a vacuum desiccator to yield 7-amino-3-(1-carboxyethyl)-1-methylpyrimido(4,5-c)-pyridazine-4,5(1H, 6H)-dione disodium salt (2.42 g; 70% of theoretical yield; m.p. >300°; hygroscopic crystals).

Elemental analysis: Calcd. for $C_{10}H_9N_5Na_2O_4.0.5\text{-}H_2O$: C, 37.74%; H, 3.17%; N, 22.01%; Na, 14.45%. Found: C, 37.69%; H, 3.21%; N, 22.05%; Na, 14.44%. nmr (TFA) δ 1.81 (d, 3H), 4.30(s, 3H), 4.45(q, 1H), 7.17(br s, 2H). uv λ max (0.1 N HCl) 255 nm (ε 41,500), 301(7,800).

B. The 3-$CH_2CH_2CO_2H$ compound (disodium salt) was prepared in a manner similar to that of 6A from the 3-$CH_2CH_2CO_2C_2H_5$ starting material except that collected precipitated solid was washed with $CH_3OH$, yield 82%. Calcd. for $C_{10}H_9N_5Na_2O_4.0.4CH_3OH.0.4\text{-}H_2O$: C, 37.94%; H, 3.49%; N, 21.27%; Na, 13.97%. Found: C, 37.91%; H, 3.21%; N, 21.36%; Na, 13.99%.

C. The 3-$CH(OCH_3)CO_2H$ compound (disodium salt) was prepared in a manner similar to that of 6A from the 3-$CH(OCH_3)CO_2C_2H_5$ starting material, yield 69%. Calcd. for $C_{19}H_9N_5Na_2O5$: C, 36.93%; H, 2.79%; N, 21.54%; Na, 14.14%. Found: C, 36.70%; H, 2.92%; N, 21.38%; Na, 14.01%.

EXAMPLE 7

3-Carbomethoxy-5,7-diamino-1-methylpyrimido(4,5-c)pyridazin-4(1H)-one (VI) ($R^2=CH_3$)

To a stirred mixture of 2,4-diamino-6-(1-methylhydrazino)pyrimidine (0.77 g) in anhydrous methanol (50 ml) was added diethyl ketomalonate (1.16 g) at room temperature. An orange solution resulted as the mixture was heated to reflux over a five minute period. After a further 72 hours of refluxing, the crude product which had separated out was collected by suction filtration of the hot mixture, washed with methanol and dried under reduced pressure at 70° C. to give a pale yellow solid (0.80 g; m.p. 272°–274° C.). Recrystallisation of 0.70 g of this solid from methanol yielded pure pale yellow 3-carbomethoxy-5,7-diamino-1-methylpyrimido(4,5-c)pyridazin-4(1H)-one (0.55 g; m.p. 274°–276° C.).

Elemental analysis: Calcd. for $C_9H_{10}N_6O_3$: C, 43.20%; H, 4.03%; N, 33.59%. Found: C, 43.12%; H, 4.05%; N, 33.54%. nmr (DMSO-$d_6$) δ 3.80 (s, 3H), 3.82 (s, 3H), 7.07 (br s, 2H), 7.90(br d, 1H, J=4 Hz), 8.80(br d, 1H, J=4 Hz). uv ($CH_3OH$) λ max 228 nm (ε 15,200), 255.5(30,300), 261 sh (29,000), 313(8,700).

EXAMPLE 8

7-Amino-3-carboxy-1-methylpyrimido(4,5-c)pyridazine-4,5(1H, 6H)-dione Disodium Salt (II) ($R^1=CO_2H$)

A mixture of 3-carbomethoxy-5,7-diamino-1-methylpyrimido(4,5-c)pyridazine-4(1H)-one (0.250 g) in 4 N aqueous sodium hydroxide (12.5 ml) was stirred at reflux for 2½ hours and then allowed to stand at room temperature for 1 hour before being filtered. The collected white solid was recrystallised twice from water/methanol, dried under vacuum at 70° C., and allowed to air-equilibrate to give 7-amino-3-carboxy-1-methylpyrimido(4,5-c)pyridazine-4,5(1H, 6H)-dione as its disodium salt (0.146 g; 45% of theoretical yield; m.p. >300° C.).

Elemental analysis: Calcd. for $C_8H_5N_5O_4Na_2.2.25\text{-}H_2O$: C, 29.87%; H, 2.98%; N, 21.77%; Na, 14.29%. Found: C, 29.60%; H, 2.60%; N, 21.54%; Na, 14.08; nmr (TFA) δ 4.30(s, 3H) 7.12(br s, 2H). uv λ max (pH 2), 266.6 nm (ε 45,700), 314.5(6,300).

EXAMPLE 9

5,7-Diamino-1,3-dimethylpyrimido(4,5-c)pyridazine-4(1H)-one (VI) ($R^2=CH_3$)

To a refluxing solution of 2,4-diamino-6-(1-methylhydrazino)pyrimidine (500 mg) in anhydrous methanol (15 ml) was added methyl pyruvate (496 mg) over a five minute period. Reflux was continued for 5 hours after which time the solid which had separated was collected by suction filtration of the hot mixture, washed with methanol, and dried under vacuum at 70° C. to yield tan crystals of 5,7-diamino-1,3-dimethylpyrimido(4,5-c)-pyridazine-4(1H)-one (508 mg; 76% of theoretical yield; m.p.>275° C.).

Elemental analysis: Calcd. for $C_8H_{10}N_6O$: C, 46.59%; H, 4.89%; N, 40.76%. Found: C, 46.66%; H, 4.98%; N, 40.69. nmr (DMSO-$d_6$) δ 2.14(s, 3H), 3.74(s, 3H), 6.84(br s, 2H)*, 7.72(br d, 1H, J=4 Hz)*, 8.96(br d, 1H, J=4 Hz)*. uv λ max ($CH_3OH$) 222 nm (λ 12,800), 247(31,100), 306(11,600).

*=exchangeable with $D_2O$.

EXAMPLE 10

7-Amino-1,3-dimethylpyrimido(4,5-c)pyridazine-4,5(1H,6H)-dione (II) ($R^1=CH_3$)

A mixture of 5,7-diamino-1,3-dimethylpyrimido(4,5-c)pyridazin-4(1H)-one (0.50 g) and 1.5 N aqueous sodium hydroxide (35 ml) was stirred at reflux for 24 hours after which time a small amount of solid was removed by filtration of the hot mixture. On cooling, the yellow filtrate deposited white needles which were collected by filtration and dissolved in warm water (20 ml). Adjustment of this aqueous solution to pH 5 by dropwise addition of 6 N hydrochloric acid and subsequent cooling to room temperature provided a very finely divided white precipitate which was collected, washed with water and dried under vacuum at 70° C. to give 7-amino-1,3-dimethylpyrimido(4,5-c)pyridazine-4,5(1H,6H)-dione (0.38 g; 76% of theoretical yield). The u.v., i.r., and n.m.r. spectra of this compound were identical to those of the sample made according to the procedure of Example 2.

EXAMPLE 11

Adopting the general procedure of Example 2, that is to say, addition of the appropriate α-ketoester of formula (V) to a refluxing mixture or solution prepared from a very pure, appropriately substituted alkylhydrazinoisocytosine of formula (IV) and filtered solvent in the proportion of 1 g in 100 ml, collected by filtration of the precipitated compound of formula (II) from the hot reaction mixture, washing with a small portion of fresh reaction solvent and drying under vacuum at 70° C., the following compounds of formula (II) were prepared:

| $R^1$ | Molar Ratio (V:IV) | Reflux Solvent & Reflux time | Yield (%) | ELEMENTAL ANALYSIS F = FOUND; Ca = CALCULATED |
|---|---|---|---|---|
| $CH(Y)CO_2Z$ Y=H, Z=$C_2H_5$ | 1.7:1 | $CH_3OH$ 48 hours | 37 | Ca: C47.31% H4.69% N25.08% F: C47.40% H4.78% N25.01% |

-continued

| R¹ | Molar Ratio (V:IV) | Reflux Solvent & Reflux time | Yield (%) | ELEMENTAL ANALYSIS F = FOUND; Ca = CALCULATED | |
|---|---|---|---|---|---|
| $CH_2C_6H_5$ | 1.1:1 | $CH_3OH$ (under $N_2$) 48 hours | 53 | Ca: F: | C59.35% H4.63% N24.72% C59.33% H4.65% N24.65% |
| $CH_2C_6H_4(NO_2)$ (2) | 1.5:1 | $CH_3OH$ 26 hours | 40 | Ca: F: | C51.22% H3.68% N25.60% C51.20% H3.71% N25.58% |
| $CH_2C_6H_3(OCH_3)_2$ (3,4) | 1.5:1 | $CH_3OH$ (under $N_2$) 42 hours | 38 | Ca: F: | C55.97% H4.99% N20.40% C56.07% H5.06% N20.27% |
| $C_6H_5$ | 1.5:1 | 1:1 $C_2H_5OH/H_2O$ 27 hours | 56 | Ca: F: | C57.99% H4.12% N26.01% C57.96% H4.17% N25.98% |
| $CH_2CH_2CO_2C_2H_5$ | 1.5:1 | $H_2O$ 2 hours | 60 | Ca: F: | C49.14% H5.16% N23.88% C49.05% H5.22% N24.07% |
| $C_2H_5$ | 1.5:1 | $CH_3OH$ 72 hours | 82 | Ca: F: | C48.86% H5.01% N31.66% C48.96% H5.00% N31.45% |
| $n-C_3H_7$ | 1.5:1 | $H_2O$ 140 minutes | 51 | Ca: F: | C51.05% H5.57% N29.77% C51.13% H5.61% N29.67% |
| $n-C_6H_{13}$ | 1.5:1 | $CH_3OH$ 48 hours | 67 | Ca: F: | C56.30% H6.91% N25.26% C56.28% H6.95% N25.17% |
| $iso-C_4H_9$ | 1.5:1 | $CH_3OH$ 48 hours | 62 | Ca: F: | C53.00% H6.07% N28.10% C53.05% H6.12% N27.97% |
| 3-Indolylmethyl | 1.2:1 | 6:1 $CH_3OH/H_2O$ 21 hours | 11 | Ca: F: | C59.62% H4.38% N26.08% C59.53% H4.41% N26.12% |
| 3-Indolyl | 1.5:1 | $CH_3OH$ 5 days | 36 | Ca: F: | C58.43% H3.92% N27.26% C58.47% H3.95% N27.14% |
| $CH(OCH_3)CO_2C_2H_5$ | 1.5:1 | $CH_3OH$ 9 days | 39 | Ca: F: | C46.60% H4.89% N22.65% C46.62% H4.93% N22.63% |
| 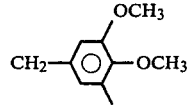 | 1.2:1 | $CH_3OH$ (under $N_2$) 50 hours | 25 | Ca: F: | C54.68% H5.13% N18.76% C54.71% H5.14% N18.81% |
| 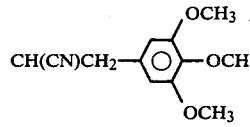 | 1.2:1 | $CH_3OH$ 166 hours | 34 (after recrystallsation from $CH_3OH$) | Ca: F: | C55.33% H4.89% N20.38% C55.11% H4.87% N20.30% |
| $CH(Y)CO_2Z$ Y=H, Z=$C_2H_5$ | 1.7:1 | $CH_3OH$ 48 hours | 37 | Ca: F: | C47.31% H4.69% N25.08% C47.40% H4.78% N25.01% |
| $CH_2C_6H_5$ | 1.1:1 | $CH_3OH$ (under $N_2$) 42 hours | 53 | Ca: F: | C59.35% H4.63% N24.72% C59.33% H4.65% N24.65% |
| $CH_2C_6H_4(NO_2)$ (2) | 1.5:1 | $CH_3OH$ 26 hours | 40 | Ca: F: | C51.22% H3.68% H25.60% C51.20% H3.71% N25.58% |
| $CH_2C_6H_3(OCH_3)_2$ | 1.5:1 | $CH_3OH$ (under $N_2$) 42 hours | 38 | Ca: F: | C55.97% H4.99% N20.40% C56.07% H5.06% N20.27% |

EXAMPLE 12

7-Amino-3-phenacyl-1-methylpyrimido(4,5-c)pyridazine-4,5(1H,6H)-dione (II) (R¹=$CH_2CO.C_6H_5$)

To a stirred, refluxing mixture of 6-(1-methylhydrazino)isocytosine hemihydrate (1.00 g) in methanol (100 ml) was added ethyl benzoylpyruvate (2.01 g). After 67 hours yellowish-brown solid was collected from the hot reaction mixture, washed with three portions of methanol totalling 20 ml, and dried under vacuum at 75° C., yield 0.130 g (7%): m.p. >300°; nmr ($CF_3COOH$) δ 4.28 (s, 3H), 4.87(s, 2H), 7.17(br s, 2H), 7.4–8.3(m, 5H); uv λ max ($CH_3OH$) 259 nm (ε 44,900), 301(8,300), 310 sh (6,900), 375 sh (900). Mass spectrum (240°): M, m/e 311, 17%; m/e 166, 1%; m/e 105, 100%. The following accurate mass was determined: 166.0487 ($C_6H_6N_4O_2$).

Anal. Calcd. for $C_{15}H_{13}N_5O_3$: C,57.87%; H,4.21%; N,22.50%. Found: C, 57.80%; H,4.26%; N,22.46%.

EXAMPLE 13

7-Amino-3-(3-hydroxyphenacyl)-1-methylpyrimido(4,5-c)pyridazine-4,5(1H,6H)-dione (II) (R¹=$CH_2CO.C_6H_4OH$)

Adopting the general procedure of Example 12, the above compound was synthesised and isolated.

Reaction time of 22 hours. Yield 7%: m.p. 290°–295° dec; nmr ($CF_3COOH$) δ 4.28 (s, 3H), 4.83 (s, 2H), 7.16(br s, 2H), 7.4–8.0(m, 4H); uv λ max ($CH_3OH$) 213.5 nm (ε 26.300), 259(47,400), 303(10,600), 309 sh (9,700).

Anal. Calcd. for $C_{15}H_{13}N_5O_4.0.5H_2O$: C,43.16%; H,5.55%; N,16.78%. Found: C,43.15%; H,5.59%; N,16.83%.

EXAMPLE 14

7-Amino-3-(2,4,6-trimethoxyphenacyl)-1-methylpyrimido(4,5-c)pyridazine-4,5(1H,6H)-dione (II) (R¹=$CH_2CO.C_6H_2(OCH_3)_3$)

Adopting the general procedures of Example 12, the above compound was synthesised and isolated.

Reaction time of 19½ hours. Yield 5%: m.p. 280° dec; nmr ($CF_3COOH$) δ 4.18, 4.24 and 4.25 (overlapping s's, 12H), 4.96(s, 2H), 6.52(s, 2H), 7.22(br s, 2H); uv λ max (CH$_3$OH) 258 nm (ε 37,500), 296.5 sh (12,700), 311.5 sh (9,800).

Anal. Calcd. for C$_{18}$H$_{19}$N$_5$O$_6$: C,53.86%; H,4.77%; N,17.45%. Found: C,53.68%; H,4.81%; N,17.46%.

EXAMPLE 15

7-Amino-3-(2,5-dimethoxyphenacyl)-1-methyl-pyrimido(4,5-c)pyridazine-4,5(1H,6H)-dione (II) (R$^1$=CH$_2$CO.C$_6$H$_3$(OCH$_3$)$_2$)

To a stirred, refluxing mixture of 6-(1-methylhydrazino)isocytosine hemihydrate (4.00 g) in methanol (400 ml) was added methyl 2,5-dimethoxybenzoylpyruvate (7.14 g). After 19 hours reddish-orange solid was collected from the hot mixture, washed with two portions of methanol totalling 50 ml, and dried under vacuum at 75° to yield 0.628 g. This solid was an inseparable 1:1 mixture of the desired 4,5-dione and its 3,5-dione isomer.

The filtrate was refluxed an additional 22.5 hours, and pale yellow solid was collected from the hot mixture, washed with several portions of methanol totalling 30 ml, and dried under vacuum at 75°, yield 0.09 g (1%): m.p. >300°; nmr (CF$_3$COOH) δ 4.02(s, 3H), 4.07(s, 3H), 4.28(s, 3H), 4.90(s, 2H), 6.8–7.7(m, 5H); uv λ max (CH$_3$OH) 223 nm weak sh (ε 22,800), 258.5(48,500), 302.5(10,000), 311.5 sh (9,000), 332.5 sh (5,500).

Anal. Calcd. for C$_{17}$H$_{17}$N$_5$O$_5$: C,54.98%; H,4.61%; N,18.86%. Found: C54.68%; H,4.64%; N,19.03%.

EXAMPLE 16

7-Amino-3-(2,4-dimethoxyphenacyl)-1-methyl-pyrimido(4,5-c)pyridazine-4,5(1H,6H)-dione (II) (R$^1$=CH$_2$CO.C$_6$H$_3$(OCH$_3$)$_2$ Following the general procedure of Example 15, the above compound was synthesised and isolated.

A 2:1 mixture of 4,5-dione and 3,5-dione isomers, respectively, was collected after 18 hours. The filtrate was refluxed an additional 47 hours for a 9% yield of 4,5-dione isomer: m.p. 290°–300° dec; nmr (CF$_3$COOH) δ 402 and 4.06 overlapping s's, (6H), 4.27(s, 3H), 4.84(s, 2H), 6.6–8.2(m, 5H); uv ε max (CH$_3$OH) 227.5 nm (ε 20,200), 259.5(40,700), 304(17,400), 413(2,800), 435(2,700), 460 (2,900).

Anal. Calcd. for C$_{17}$H$_{17}$N$_5$O$_5$: C,54.98%; H,4.61%; N,18.86%. Found: C,54.97%; H,4.69%; N,18.98%.

EXAMPLE 17

7-Amino-3-(3,4-dimethoxyphenacyl)-1-methyl-pyrimido(4,5-c)pyridazine-4,5(1H,6H)-dione (II) (R$^1$=CH$_2$CO.C$_6$H$_3$(OCH$_3$)$_2$ Following the general procedure of Example 15, the above compound was synthesised and isolated.

An insoluble mixture was collected after 17 hours. The filtrate was refluxed an additional 47 hours for a 2% yield of 4,5-dione isomer: m.p. >300°; nmr (CF$_3$COOH) δ 4.04 and 4.08 (overlapping s's, 6H), 4.28(s, 3H), 4.83 (s, 2H), 7.0–7.4(m, 3H), 7.7–8.2(m, 2H); uv λ max (CH$_3$OH) 229 nm (ε 23,300), 259(42.000), 274 sh (22,200), 304 (18.700).

Anal. Calcd. for C$_{17}$H$_{17}$N$_5$O$_5$.0.1H$_2$O: C,54.72%; H,4.65%; N,18.77%. Found: C,54.71%; H,4.68%; N,18.71%.

EXAMPLE 18

7-Amino-3-(3,4,5-trimethoxyphenacyl)-1-methyl-pyrimido(4,5-c)pyridazine-4,5(1H,6H)-dione (II) (R$^1$=CH$_2$CO.C$_6$H$_2$(OCH$_3$)$_3$ Following the general procedure of Example 15, the above compound was synthesised and isolated.

A 1:1 mixture of 4,5-dione and 3,5-dione isomers, respectively, was collected after 18½ hours. The filtrate was refluxed an additional 23 hours for a 2% yield of 4,5-dione isomer: m.p. >300°; nmr (CF$_3$COOH) δ 4.07 and 4.13 (overlapping s's, 9H), 4.30(s, 3H), 4.86(s, 2H), 7.18(br s, 2H), 7.54(s, 2H); uv λ max (CH$_3$OH) 213 nm (ε 32,500), 258.5(43.700), 297 sh (17,200), 310 sh (13,700). Mass spectrum (250°): M, m/e 401, 7%; m/e 195, 100%; m/e 166, 2%. The following accurate mass was determined: 166.0488 (C$_6$H$_6$N$_4$O$_2$).

Anal. Calcd. for C$_{18}$H$_{19}$N$_5$O$_6$: C,53.86%; H, 4.77%; N,17.45%. Found: C,53.82%; H,4.85%; N,17.55%.

EXAMPLE 19

Potential inhibitors of DHPB synthesis may be tested by investigating the inhibitory effect they impose in the enzymes responsible for the biosynthesis of dihydropteroic acid (DPtA), namely hydroxymethyldihydropteridine pyrophosphokinase (HMPPS), and dihydropteroate synthetase, hereinafter referred to as 'synthetase'. In the following reaction equations the compounds are referred to by their abbreviated forms defined hereinbefore in the specification.

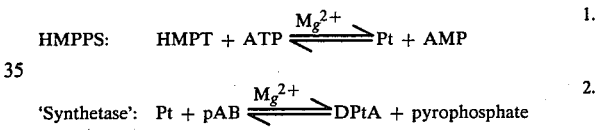

1. HMPPS: HMPT + ATP $\underset{}{\overset{Mg^{2+}}{\rightleftharpoons}}$ Pt + AMP 2. 'Synthetase': Pt + pAB $\underset{}{\overset{Mg^{2+}}{\rightleftharpoons}}$ DPtA + pyrophosphate This reaction requires two enzymes since the starting substrates are H$_2$ptCH$_2$OH, ATP, and pAB, and the products are H$_2$pteroate and AMP. In crude extracts of E. coli (and the 0–50% ammonium sulfate fraction used by us) the first enzyme, 2-amino-4-hydroxy-6-hydroxymethyl-7,8-dihydropteridine pyrophosphokinase ("kinase"), has a threefold lower specific activity than the second enzyme, dihydropteroate synthetase ("synthetase").

The reactions are followed by determining the amount of $^{14}$C in H$_2$pteroate after separation from the substrate, p-aminobenzoate-7-$^{14}$C, by paper chromatography.

The following results were obtained by the coupled assay method.

| Compound of formula (II) R$^1$ | Concentration in μM required to give 50% inhibition of DHPB |
|---|---|
| CH$_3$ | 16.0 |
| C$_6$H$_5$ | 15.0 |
| CH$_2$OH | 12.0 |
| CH$_2$OCOCH$_3$ | 15.0 |
| CO$_2$H (disodium salt) | 21.0 |
| CH(CH$_3$)CO$_2$C$_2$H$_5$ | 1.6 |
| CH(CH$_3$)CO$_2$H | 3.7 |
| CH$_2$CH$_2$CO$_2$H | 5.5 |
| CH$_2$CH$_2$CO$_2$C$_2$H$_5$ | 16.0 |
| C$_2$H$_5$ | 33.0 |
| CH$_2$C$_6$H$_5$ | 11.0 |
| n-C$_3$H$_7$ | 45.0 |
| n-C$_6$H$_{13}$ | 50.0 |

-continued

| Compound of formula (II) R¹ | Concentration in μM required to give 50% inhibition of DHPB |
|---|---|
| iso-$C_4H_9$ | 20.0 |
| $CH_2$–C₆H₄–NO₂ | 12.0 |
| 3-Indolylmethyl | 3.0 |
| 3-Indolyl | 30.0 |
| $CH_2CO_2C_2H_5$ | 6.2 |
| $CH(OCH_3)CO_2C_2H_5$ | 17.0 |
| $CH(OCH_3)CO_2H$ | 2.8 |
| $CH_2COC_6H_5$ | 0.76 |
| $CH_2CO$–C₆H₃(OCH₃)₂ (2,3-dimethoxy) | 0.15 |
| $CH_2CO$–C₆H₂(OCH₃)₃ (3,4,5-trimethoxy) | 0.03 |
| $CH_2CO$–C₆H₃(OCH₃)₂ (3,5-dimethoxy) | 0.14 |
| $CH_2$–C₆H₃(OCH₃)₂ | 0.77 |

-continued

| Compound of formula (II) R¹ | Concentration in μM required to give 50% inhibition of DHPB |
|---|---|
| $CH_2CO$–C₆H₃(OCH₃)₂ (3,4-dimethoxy) | 0.06 |
| $CH_2CO$–C₆H₂(OCH₃)₄ | 2.7 |
| $CH_2CO$–C₆H₄(OH) | 0.22 |
| $CH_2$–C₆H₂(OCH₃)₃ | 0.86 |
| $CH(CN)CH_2$–C₆H₂(OCH₃)₃ | 11.0 |

What is claimed is:
1. A compound of the formula (VIII):

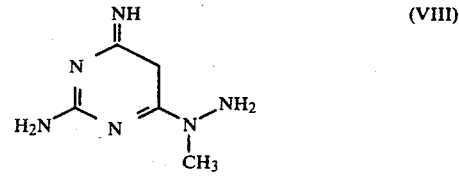

(VIII)

tautomers thereof and salts thereof.

* * * * *